United States Patent
Moura et al.

(10) Patent No.: US 7,788,112 B2
(45) Date of Patent: Aug. 31, 2010

(54) PHARMACEUTICAL MARKETING DEVICE AND METHOD

(76) Inventors: Eden Ferreira Moura, 10301 Lynnhaven Pl., Oakton, VA (US) 22124; Eric Ronald Sharp, 11207 Sandusky Ct., Fredericksburg, VA (US) 22407

( * ) Notice: Subject to any disclaimer, the term of this patent is extended or adjusted under 35 U.S.C. 154(b) by 1263 days.

(21) Appl. No.: 11/288,272

(22) Filed: Nov. 29, 2005

(65) Prior Publication Data

US 2007/0124172 A1   May 31, 2007

(51) Int. Cl.
*A61B 5/00* (2006.01)
*G06F 19/00* (2006.01)
*G06Q 10/00* (2006.01)
*G06Q 50/00* (2006.01)
*G06Q 30/00* (2006.01)

(52) U.S. Cl. ................ 705/2; 705/3; 705/14.4
(58) Field of Classification Search .................. None
See application file for complete search history.

(56) References Cited

U.S. PATENT DOCUMENTS

| | | |
|---|---|---|
| 5,628,530 A | 5/1997 | Thornton |
| 5,961,151 A | 10/1999 | Tung |
| 6,604,085 B1 * | 8/2003 | Kolls ........................... 705/14 |
| 2002/0032582 A1 * | 3/2002 | Feeney et al. .................. 705/2 |
| 2002/0035484 A1 | 3/2002 | Mccormick |
| 2002/0042762 A1 | 4/2002 | McQuade et al. |
| 2002/0065683 A1 | 5/2002 | Pham et al. |
| 2002/0184072 A1 | 12/2002 | Linde et al. |
| 2003/0088442 A1 * | 5/2003 | Michael et al. ................ 705/3 |
| 2004/0015417 A1 * | 1/2004 | Youngman et al. ............ 705/27 |
| 2004/0236630 A1 | 11/2004 | Kost et al. |

OTHER PUBLICATIONS

"Savage Laboratories Chooses Dendrite's ForcePharma." Business Wire. Business Wire. 1999. HighBeam Research. Jun. 4, 2010 <http://www.highbeam.com>.*

* cited by examiner

*Primary Examiner*—Luke Gilligan
*Assistant Examiner*—Eliza Squires
(74) *Attorney, Agent, or Firm*—Volentine & Whitt, PLLC

(57) ABSTRACT

A healthcare professional enters signature data into a signature capture device upon receipt of a pharmaceutical product. The signature capture device receives the signature data and displays a promotional message for the pharmaceutical product while receiving the signature data.

20 Claims, 9 Drawing Sheets

PHARMACEUTICAL MARKETING DEVICE AND METHOD

BACKGROUND OF THE INVENTION

1. Field of the Invention

Embodiments of the present invention relate generally to a device and associated method for promoting prescription drugs to healthcare professionals. More particularly, embodiments of the invention relate to a device and method adapted to display promotional message data relating to a specific drug in response to receiving signature data from the healthcare professional.

2. Description of Related Art

Pharmaceutical companies employ an immense workforce of representatives who seek to promote company products to healthcare professionals and other healthcare professionals. (Hereafter, the term "healthcare professional" will be generally used throughout this description to denote any person providing medical or healthcare services, including without limitation healthcare professionals of all specialties, and other individuals acting under a healthcare professional's supervision or authority, or acting in conjunction with a healthcare professional, including without limitation; assistants, nurses, technicians, dietitians, front-office staff, etc.). Perhaps the largest and most expensive part of a representative's promotional efforts focus on providing drug samples to healthcare professionals and encouraging healthcare professionals to write more prescriptions for the sampled drugs.

Pharmaceutical companies spend enormous amounts of time and money educating pharmaceutical representatives about the companies' products and training them how to interact with healthcare professionals. For instance, the cost of training a single pharmaceutical representative may range up to $200,000 and require several months to complete. In addition these significant training costs, pharmaceutical companies compensate their representatives with generous salaries and benefits, and bonuses in order to encourage performance.

Unfortunately, the typical healthcare professional has little time to interact with pharmaceutical representatives. Healthcare professionals commonly restrict such interactions, often allowing only passing visits (e.g., 30 second to 2 minute) in a hallway between patient appointments. Often, the healthcare professional's sole motivation for allowing even these brief visits is the receipt of drug samples. However, government regulations require that the healthcare professional sign for any drug samples received. Thus, in extreme cases, a busy healthcare professional may sign for drug samples without any substantive interactions with a pharmaceutical representative.

Needless to say, these brief or non-existent interactions with a healthcare professional do not allow the pharmaceutical representative much of an opportunity to promote the companies' products. Thus, in many instances, the highly-trained pharmaceutical representative is little more than an expensive delivery person for drug samples.

One technique used by pharmaceutical representatives to compensate for their lack of quality face time with healthcare professionals is one of leaving behind promotional materials or marketing items such as product catalogs, books, charts, notepads, pens, mugs, and so forth. Ideally, these promotional items are tailored to a particular healthcare professional's practice or needs. In general, the promotional items serve both to educate the healthcare professional about particular drugs, and to entice the healthcare professional to prescribe more of the drugs.

Unfortunately, the time honored approach of leaving behind promotional materials has significant shortcomings. First, because the needs and/or wants of each respective healthcare professional are not generally known, pharmaceutical companies supply each representative with literally thousands of pounds of assumedly "most relevant" promotional items. This is very expensive and dramatically inefficient. Second, promotional materials provided by pharmaceutical companies require approval from the Food and Drug Administration (FDA) before they can be distributed to healthcare professionals. As a result, there is generally a significant lag time between approval of new promotional materials and their actual availability to pharmaceutical representatives. The lag time translates into lost marketing opportunities.

In addition to the problems posed by lack of face time with healthcare professionals, pharmaceutical representatives are also burdened with a responsibility of adhering to strict FDA standards. Broadly speaking, the relevant standards deal with (1) the content of a pharmaceutical representative's presentation to healthcare professionals, and (2) proper documentation regarding the distribution of drug samples.

The content of a pharmaceutical representative's presentation to healthcare professionals is closely regulated by the FDA. In particular, the FDA must approve all major claims made regarding a drug. In adherence to this policy, pharmaceutical representatives generally base their presentations on a "master visual aid" (MVA) prepared by the pharmaceutical company and approved by the FDA beforehand. The MVA typically includes therapeutic claims related to the drug, together with relevant pictures and supporting data (e.g., graphs, charts, text boxes, etc.). Failure to adhere to the FDA's guidelines governing the content of a pharmaceutical representative's presentations can result in serious legal penalties.

The regulations governing the documentation of drug sample distributions by a pharmaceutical representative are laid out, for example, in 21 C.F.R. §203.31. Upon delivery of drug samples to a healthcare professional (i.e., a "licensed practitioner"), or a healthcare professional's designee, the pharmaceutical representative must obtain the healthcare professional's or his/her designee's signature on a receipt containing information such as the healthcare professional's name, address, title, state license number, the quantity of the drug and so forth. The pharmaceutical representative uses this information to maintain mandatory inventory records for the pharmaceutical company. Historically, maintaining the receipts and inventories has been a significant burden on pharmaceutical representatives. Moreover, the receipts and inventories maintained by each pharmaceutical representative are commonly audited to make sure that the information is correct, and to verify that the person who signed for the drug samples is actually the healthcare professional or his/her authorized designee. This leads to even greater overhead and expense for the pharmaceutical company.

Some of the documentary burden placed on pharmaceutical representatives has been lifted through the use of technology such as computers, PDAs, and the Internet. For example, U.S. Patent Application Publication No. 2003/0088442 discloses a mobile computing device adapted to electronically capture a healthcare professional's signature upon delivery of drug samples, thus obviating the pharmaceutical representative's need to manage unwieldy receipt paperwork. The mobile computing device maintains a local inventory of the pharmaceutical representative's drug samples, and it can communicate with other mobile devices or a main database to transfer information about the overall distribution of drug samples. The mobile computing device is also equipped with a bar-code scanner for scanning drug samples when they are delivered.

Similar devices are disclosed in various commercial embodiments such as "Siebel Pharma Handheld", "AvantGo Mobile Pharma", and "Dendrite SampleEnforcer™." All of these devices allow healthcare professionals or their designees to sign for drug samples on a mobile computing device, and additionally they provide various software applications to make the pharmaceutical representatives' lives more convenient. For instance, some of these commercial devices store healthcare professional profiles and schedules, they keep track of sample orders, inventories. They also allow new orders to be taken wirelessly.

Other technical advances allow healthcare professionals to browse through promotional information about pharmaceutical products on a computer instead of relying wholly on presentations from a pharmaceutical representative. For instance, Patent Application Publication No. 2002/0035484 (the '484 Application) discloses a mobile computing device used by healthcare professionals to write prescriptions. The handheld device stores a database containing educational or advertising information regarding specific drugs and other information originated from a drug company. The healthcare professional can browse through this information and prescribe drugs for patients through the device by biometrically authenticating the healthcare professional's identity through the device, (e.g., by a signature, a voice print, etc).

Unfortunately, these technology solutions fail to successfully address the pharmaceutical representative's most pressing problem—the lack of quality face time with the healthcare professional. Clearly, the opportunity to directly and specifically market their products to a healthcare professional is highly coveted by pharmaceutical companies—hence, the great expense and effort involved in hiring and training representatives and providing them with state-of-the art technology. Unfortunately, such expense and effort often fail to yield the desired result—a clear, timely, FDA-compliant, and targeted advertising pitch to the healthcare professional.

SUMMARY OF THE INVENTION

In one embodiment, the invention provides a method of communicating information to a healthcare professional, the method comprising; capturing signature data from the healthcare professional in a signature capture device, and in response to the signature data, communicating a promotional message data related to a pharmaceutical product through the signature capture device. In a related aspect, the foregoing method may further comprise; providing a drug sample to the healthcare professional, wherein capturing signature data is performed in relation to providing the drug sample to the healthcare professional.

In another embodiment, the invention provides a signature capture device, comprising; a signature interface adapted to capture signature data from a healthcare professional, and a communications interface adapted to communicate promotional message data related to a pharmaceutical product in response to capturing the signature data. In one related aspect, the communications interface may begin to communicate the promotional message data after the interface captures the signature data, in another related aspect the communications interface begins to communicate the promotional message data before the interface captures the signature data.

In another embodiment, the invention provides a method of communicating information on a signature capture device comprising a signature interface and a communications interface, the method comprising; receiving signature data in the signature capture device via the signature interface, and in response to receiving the signature data in the signature capture device, communicating promotional message data on the communications interface. In one related aspect, the signature area may comprise; an address for a pharmaceutical company providing drug samples, a time and date, a name of a healthcare professional, a number identifying the healthcare professional, an identification and quantity of drug samples, a statement that the healthcare professional is authorized to receive the drug samples, and a signature block where the healthcare professional enters signature data.

BRIEF DESCRIPTION OF THE DRAWINGS

The invention is described below in relation to several embodiments illustrated in the accompanying drawings. In the drawings.

DESCRIPTION OF EXEMPLARY EMBODIMENTS

Figure 1:
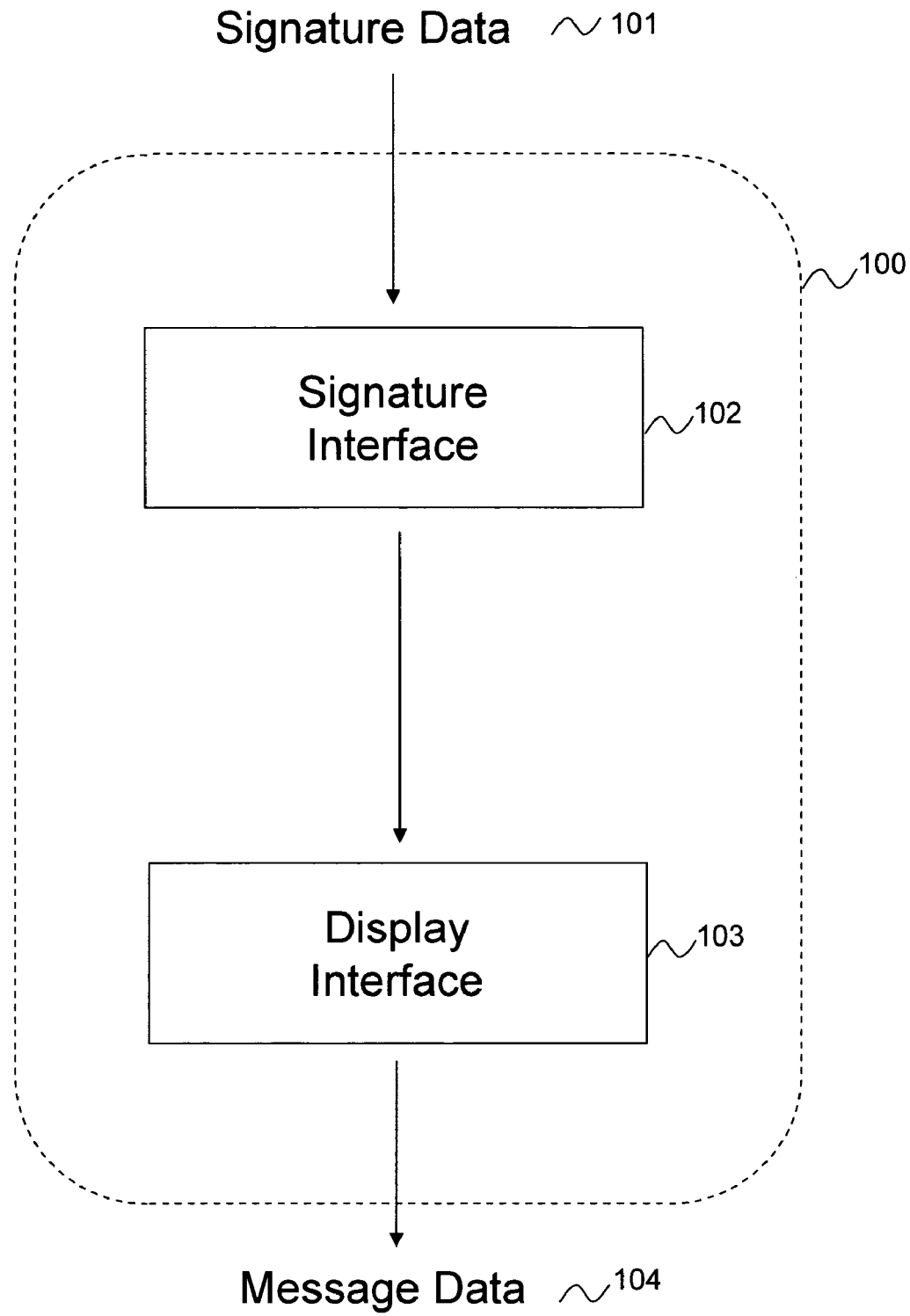
FIG. 1 is a block diagram of a signature capture device according to an embodiment of the present invention.

Exemplary embodiments of the invention are described below with reference to the corresponding drawings. These embodiments are presented as teaching examples. The actual scope of the invention is defined by the claims that follow.

Briefly, embodiments of the invention address the problem of delivering a promotional message related to pharmaceutical products to a healthcare professional by displaying the promotional message during an electronics-based healthcare professional signature capture operation. That is, a promotional message is communicated visually and/or audibly to the healthcare professional during the signature process required to receive drug samples or some other related process. A pharmaceutical representative provides a competent signature capture device to the healthcare professional when delivering drug samples. Before, during, or after initiating a signature process, the signature capture device communicates the promotional message.

In this description, the term "healthcare professional" further denotes any person authorized to sign for drug samples. For example, the "healthcare professional" could be any person authorized to sign under 21 U.S.C. §203.30 or 21 U.S.C. §203.31 or similar regulatory framework. Typically, the healthcare professional is a healthcare professional; however, the healthcare professional may designate another party to sign for drug samples.

The term "pharmaceutical representative" denotes any person authorized to deliver drug samples to a healthcare professional on behalf of a pharmaceutical company. Although pharmaceutical representatives generally have special training and are under an employer/employee relationship with the pharmaceutical company, the term is used more generically within this description. In other words, any person who delivers drug samples on behalf of the pharmaceutical company may be considered a "pharmaceutical representative" within the context of the following embodiments.

The term "drug sample" is defined as a unit of a prescription drug that is not intended to be sold, but is intended to promote the sale of the drug. (See, 21 U.S.C. §203.3(i)). Drug samples are commonly distributed with bar code identifiers to track their location, use, and transfer from person to person, (e.g., from pharmaceutical representative to healthcare professional or between pharmaceutical representatives).

The term "pharmaceutical product" refers to any items sold or distributed by a pharmaceutical company. For example, prescription drugs, promotional or non-promotional literature, drug samples, and so forth, are all considered pharmaceutical products.

The term "signature" denotes any type of personal identifier, including without being limited thereto, a handwritten signature, an electronic signature, a biometric signature, and any equivalent thereof. The term "electronic signature" is defined as any computer data compilation of symbols or series of symbols executed, adopted, or authorized by an individual to be the legally binding equivalent of his/her handwritten signature. (See, 21 U.S.C. §203.3(I)). The term "biometric signature" refers to a unique identifier of an individual based on the person's physical attributes and used to authenticate the individual. For example, a biometric signature could comprise a person's fingerprint, voiceprint, retinal pattern, bone density, and so forth.

The term "signature data" refers to any portion, putative portion, or prospective portion of a signature. For instance, if a person touches a stylus to a signature area in an electronic signature capture device, the device begins to capture "signature data." Even if the signature data does not result in an actual signature being captured, a signature capture device may initiate some operation based on receiving the signature data. In general, a completed signature comprises a collection of signature data.

The term "signature capture device" denotes any device capable of capturing signature data and displaying a promotional message in response to capturing the signature data. In general, a signature capture device comprises a computational platform including at least a processor and memory, a "signature interface" adapted to capture the signature data, and a "display interface" adapted to display the promotional message. Examples of signature capture devices include personal digital assistants (PDAs), tablet computers, laptop computers, and so forth.

The signature capture device is typically configured to operate in coordination with peripheral input or output devices, such as a mouse, a stylus, a printer, an external monitor, a projector, etc. In addition, the signature capture device generally includes various software or hardware applications dedicated to receiving and processing the signature data. For instance, if the signature is a biometric signature or an electronic signature, the signature capture device generally engages in some type of decoding or recognition procedure.

The signature data can be captured through any of various conventional input technologies, including, for example, a stylus making contact with a capacitative or resistive sensor, a microphone receiving voice data, a radio frequency identification (RFID) sensor capturing an electronic signature, a camera sensing a retinal pattern, or a capacitative sensor or camera sensing a fingerprint. In each case, the signature interface is the portion of the signature capture device that acts to receive the signature data. Upon receiving the signature data or a completed signature, the signature capture device processes the signature data or completed signature and/or stores it in memory. In addition to receiving signature data, the above input technologies can also be used to receive data for generally controlling the signature capture device.

The promotional message may be communicated through any of a number of conventional interfaces, such as a speaker, a screen, a printer, etc. In one embodiment, the promotional message may include an invitation to the healthcare professional or instructions regarding involvement in a teleconference, a video conference, a so-called "ready conference", or similar marketing event. The term "communicate" denotes any process of conveying information through a signature capture device, including the visual display of graphics or text on the screen, transmission of an audio file through the speaker, and/or the output of printed materials, graphics and/or text through the printer, etc.

Those skilled in the art will understand that the signature capture device and its associated signature interface and communications interface may be variously embodied, and therefore, an exhaustive list of these technologies is omitted from this description. Such devices and interfaces span a wide range of computer technology, mobile computing devices, and input/output (I/O) interfaces types.

Preferably, the signature capture device is capable of communicating with a server computer through a wired and/or wireless network connection. Such a connection allows the signature capture device to perform functions such as downloading and uploading files, verifying captured signatures against a central database, updating centralized inventory records, etc. Additionally, the signature capture device may contain a tracking device such as a global positioning system (GPS) to track the location of the pharmaceutical representative. Furthermore, the signature capture device may also include a bar code scanner or similar device adapted to identify, register and/or track drug samples.

The term "signature process", or alternatively "sign", generally denotes actions performed by a person or devices to transfer a signature or signature data to a signature capture device. For instance, a signature process is performed when a healthcare professional signs (in written style) a signature capture device with a stylus, when a RFID sensor detects an electronic signature from a device carried by the healthcare professional, and/or when a person submits him or herself to a biometric measurement, etc. A person is said to "sign" a signature capture device when the person or a device associated with the person performs actions to transfer a signature or signature data to a signature capture device.

The term "promotional message" refers to a presentation, (e.g., a multimedia presentation) generated by the signature capture device in response to receiving signature data. In this context, the phrase "in response to receiving signature data" is not limited to a time period or sequence in which a promotional message is communicated only after the physical act if signing has begun. Rather, the promotional message may be responsively communicated in and around the time the signature capture device is presented to the healthcare professional, up to and including the time the signature capture device is returned to the pharmaceutical representative.

The term "promotional message data" refers to data related to the promotional message, or any part of the promotional message. Promotional message data may include any combination of text, graphics, animations, audio, video, and so forth, where the term "graphics" encompasses any form of graphical art, such as photographs, drawings, virtual models, and the like.

The promotional message may be interactive, meaning that it may allow a healthcare professional to select information that he or she wants to see or hear or to enter data such as orders for pharmaceutical products, answers to survey questions, and responses to invitations to pharmaceutical industry events. The signature capture device preferably comprises a user interface such as a graphical user interface adapted to receive interactive user inputs, or other commands, from the healthcare professional to communicate specific information regarding a particular drug.

The promotional message to-be-communicated may be chosen from a collection of promotional messages, either residing in the signature capture device, or downloaded from a wired and/or wireless network connection. The choice of a particular promotional message to-be-communicated may be determined by each pharmaceutical representative or by an automated procedure run from a central office. For example, the pharmaceutical representative could select a particular message before a visit based on his/her knowledge of a healthcare professional's prescribing habits or practice. Alternatively, an automated procedure could similarly select the promotional message to-be-communicated based on centralized information, such as drug samples previously delivered, practice history, past company interactions with the healthcare professional, etc. Alternatively, the healthcare professional could choose a promotional message to be communicated.

The collection of promotional messages will contain promotional information already approved by the company and/or the FDA. To ensure that this is the case, the collection of promotional messages will be updated periodically by the pharmaceutical company. These updates can be made by an automated procedure or in response to a query from the pharmaceutical representative.

FIG. 1 is a block diagram of a signature capture device 100 according to one embodiment of the present invention. Referring to FIG. 1, signature capture device 100 comprises a signature interface 102 and a communications interface 103. Signature capture device 100 receives signature data 101 from a healthcare professional through signature interface 102 and outputs (or displays) promotional message data 104 through communications interface 103 in response to the signature data 101.

Signature capture device 100 may begin communicating promotional message data 104 upon receiving signature data 101, for example, when a stylus contacts signature interface 102. Alternatively, promotional message data 104 may be communicated after a pre-set delay following receipt of signature data 101. The delay could begin either immediately upon receiving signature data 101, or after a complete signature is received and/or verified. As a further alternative, signature capture device 100 may begin communicating promotional message data 104 before receiving signature data 101. For instance, signature capture device 100 could communicate a looping or static promotional message as the healthcare professional receives that signature capture device 100. The desired promotional message may be selected and/or set up by the pharmaceutical representative before his/her visit to the healthcare professional.

Figure 2:
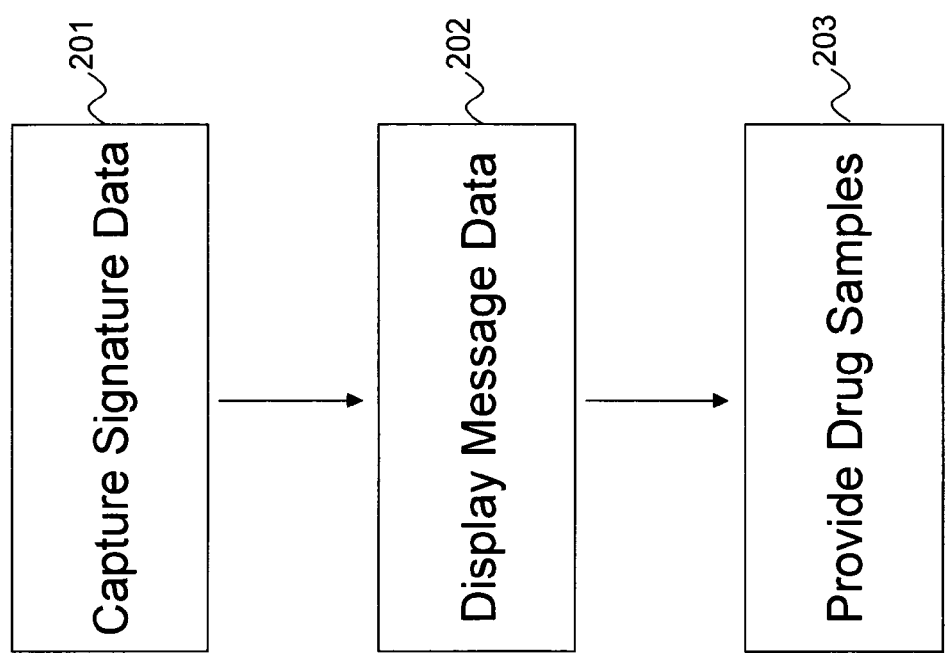
FIG. 2 is a flowchart illustrating a method of providing a drug sample to a healthcare professional according to an embodiment of the present invention.

FIG. 2 is a flowchart illustrating a method of communicating information about a pharmaceutical product to a healthcare professional according to one embodiment of the present invention. In this written description, exemplary method steps are denoted by parentheses (XXX) to distinguish them from exemplary system or device elements such as those in FIG. 1.

Referring to FIG. 2, the method comprises providing a drug sample to a healthcare professional (201), capturing signature data from the healthcare professional in a signature capture device upon providing the drug sample to the healthcare professional (202), and displaying promotional message data through the signature capture device while capturing the signature data in the signature capture device (203). However, as noted above, the promotional message data may be communicated by the signature capture device before, during or after capturing the signature data in the signature capture device.

Figure 3:
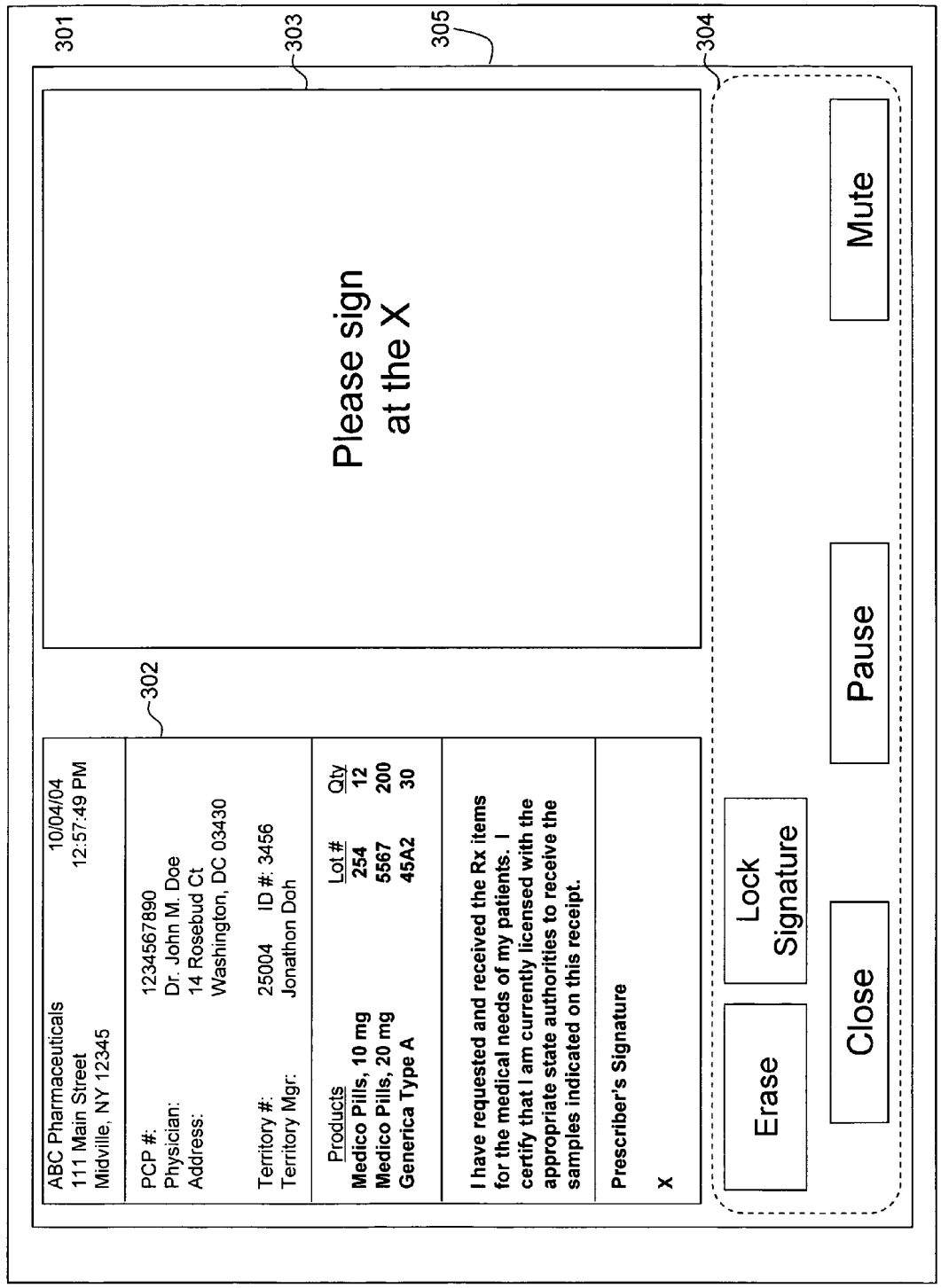
FIG. 3 is a block diagram of a signature capture device according to another embodiment of the present invention.

FIG. 3 is a block diagram of an exemplary signature capture device 300 according to another embodiment of the present invention. Referring to FIG. 3, signature capture device 300 comprises a tablet computer 301 having a screen 305 with a graphical user interface (GUI) divided into a signature area 302 and a message area 303. The GUI for screen 305 may also include a user interface area 304 including a plurality of software programmable buttons (i.e., "hot links") for controlling signature capture device 300. Alternatively, a physical interface, such as a keyboard or stylus key pad, may be provided in place of the screen programmable user interface area 304.

Signature area 302 may generally include the name and address of the pharmaceutical company providing drug samples, the time and date of a drug sample delivery and corresponding signature, an identifying number (e.g., a primary care physician or PCP number) for the healthcare professional, the healthcare professional's name and address, a territory number and identification number for the pharmaceutical representative, and the name of the pharmaceutical representative's supervising manager. Signature area 302 further includes identification and quantity of drug samples being delivered, a regulatory statement that the healthcare professional is authorized to receive the drug samples, and a signature block where the healthcare professional signs for the drug samples. In addition, signature area 302 may further include a statement of acknowledgment of terms contained in various documents related to the distribution of the drug samples, such as an "Adverse Reaction Report", a "Drug Information Services Request", or a "Drug Interaction Report". Once the healthcare professional signs the signature block, the information contained in signature area 302 may be saved as a "signed electronic document" that can thereafter be viewed from a "view signatures screen," described below.

Message area 303 is used to communicate the promotional message. Message area 303 may initially contain instructions for the healthcare professional to sign the signature block. However, message area 303 may also contain a looping or static promotional message being communicated as the healthcare professional receives the signature capture device. Once the healthcare professional begins signing signature area 302, or following a delay after the healthcare professional begins signing, message area 303 will communicate a promotional message. Where a looping promotional message or a static promotional message was previously communicated in message area 303, the same message may continue, or a new message may be communicated upon signature initiation and/or completion.

Signature capture device 300 may also comprise a speaker communicating an audio portion of the promotional message being visually communicated in message area 303.

In one embodiment, user interface area 304 includes a plurality of "hot links" for controlling software application(s) running on the signature capture device 300. For instance, user interface area 304 may include an erase button for clearing the signature block, a lock signature button for saving the information in the signature area 302, a close button for terminating the software application, a pause button for pausing the promotional message, and/or a mute button for muting the promotional message. The foregoing are just selected examples of user interface controls that may be provided by the signature capture device. Such controls will vary by device and application.

FIGS. 4 through 9 are flowcharts illustrating various methods of operating embodiments of the invention, such as the one shown in FIG. 3. In particular, the methods illustrated in FIGS. 4 through 9 allow a user to navigate through the GUI provided by screen 305 to show different screens, run different applications, set options, and so forth. In the description that follows, the term "user" refers to anyone who uses signature capture device 300. The user is generally a pharmaceutical representative, but it could also be a healthcare professional, a technician, or anyone else within proximity of the device.

Figure 4:
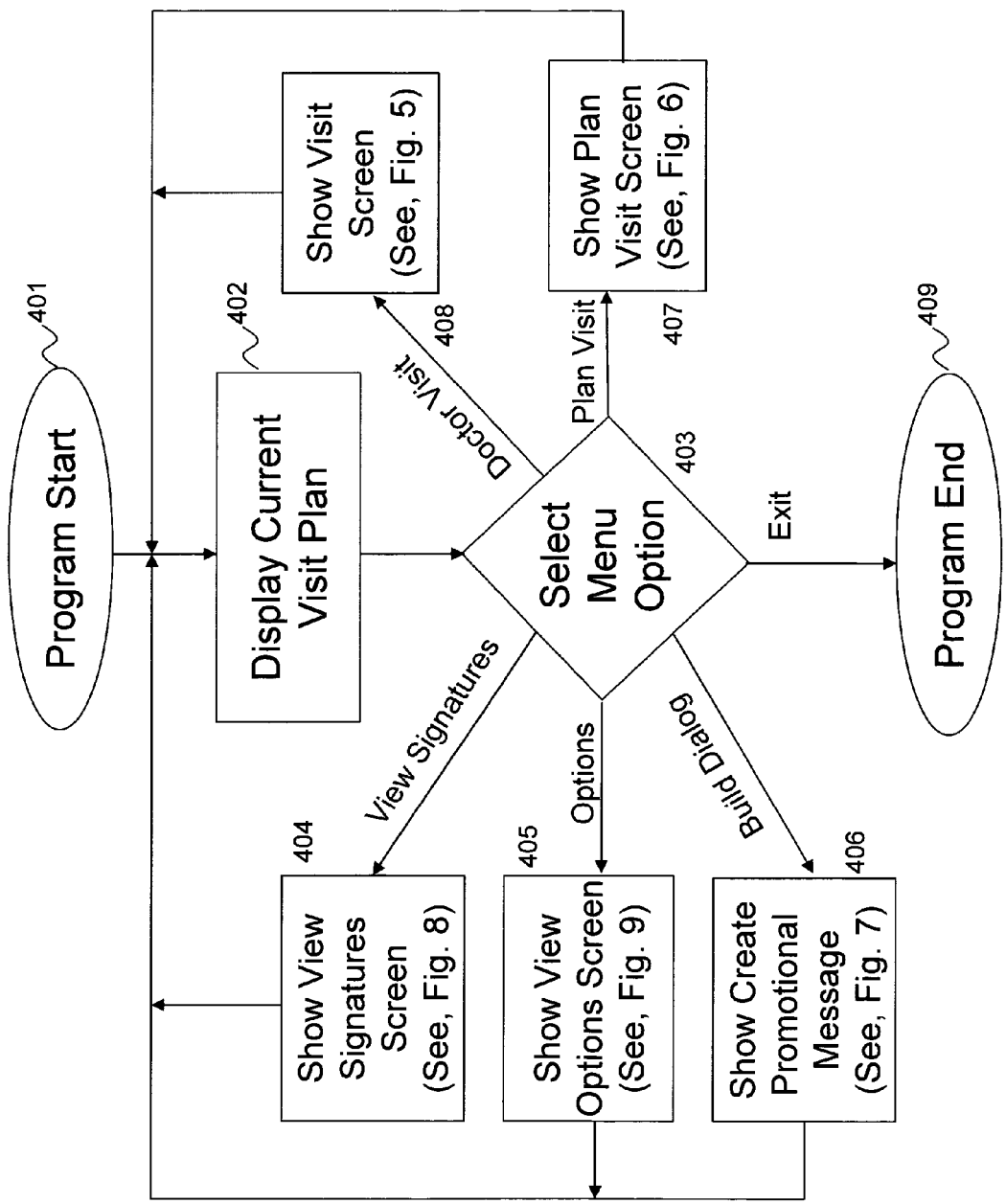
FIGS. 4 through 9 are flowcharts illustrating various methods of operating the signature capture device shown in FIG. 3.

Referring to FIG. 4, a main application runs on signature capture device 300 (401). Once the main application starts, the GUI displays a "main menu screen" including a "current visit plan" and a menu (402).

The current visit plan comprises information for planning a visit to a particular healthcare professional. The current visit plan typically includes a list of drug samples to be given to the healthcare professional, information about the healthcare professional, and a particular (or targeted) promotional message to be presented to the healthcare professional during the visit.

The menu contains several options for navigating through the main application. A user selects among these options (403) to go to various screens within the main application. In particular, by selecting a "view signatures" option, the user goes to a "signatures screen" (404). By selecting an "options" option, the user goes to a "view options screen" (405). By selecting a "build promotional message" option, the user goes to a "build promotional message screen" (406). By selecting a "healthcare professional visit" option, the user goes to a "visit screen" (408). By selecting a "plan visit" option, the user goes to a "plan visit screen" (407). Finally, by selecting an "exit" option, the user terminates the main application. After going to any of the "screens" selected through the menu, a user can generally choose to return to the main menu screen.

The "visit screen" is communicated to the healthcare professional during a visit by the pharmaceutical representative. The "visit screen" is used to capture the healthcare professional's signature and communicate the promotional message.

The "plan visit screen" is used by the pharmaceutical representative or other company employee to plan details of a visit, such as which specific healthcare professional to visit, what to discuss during the visit, what promotional message to communicate, what drug samples to distribute, etc.

The "build promotional message screen" allows the user to create a promotional message based on a set of predefined promotional message elements. The promotional message elements could include, for example, specific graphs, charts, text items, videos, sound bytes, etc.

The "view signatures screen" lets the user view signed electronic documents. The user may want to see the "view signatures screen," for example, to review all the drug samples that have previously been distributed to a particular healthcare professional, or by the pharmaceutical representative during a defined period of time.

The "options screen" allows the user to change various aspects of the main application such as the way it displays graphics, what information it stores about the pharmaceutical representative, and what hot links are used by various screens in button area 304.

Figure 5:
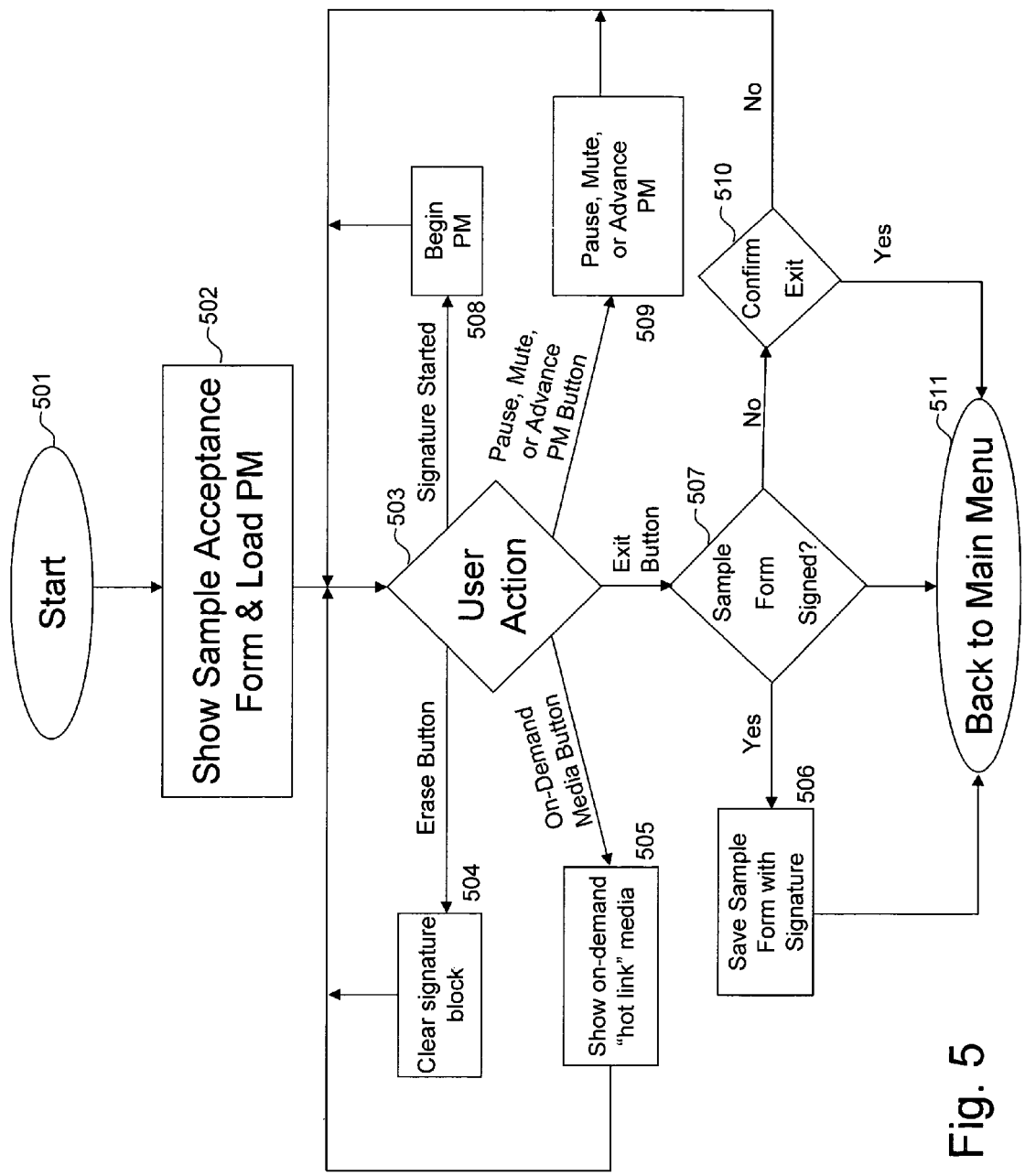

Referring to FIG. 5, in the "visit screen," a sample acceptance form is displayed in signature area 302 and a promotional message is loaded by the main application (502). A user performs a "user action" in the context of the visit screen to initiate one of several processes (503). The user action may comprise, for example, touching signature capture device 300 with a stylus to press one of the hot links in button area 304, signing the signature block in signature area 302, or issuing a voice command.

Where the user begins to sign the signature block, the promotional message is communicated in response thereto in message area 303 (508). Where the user presses the erase button, the signature block is cleared (504). Where the user presses the pause or mute button or an "advance promotional message" button, the promotional message pauses, mutes, or advances (509). Where the user presses an on-demand media button, the message area shows a promotional message that may be different from the one that plays automatically when a signature is entered in the signature block. Finally, when the user presses the exit button, the main application returns to the main menu screen after confirming that the signature block has been signed (506) or that the user wishes to exit the visit screen (510). Whenever the user presses one of the buttons in button area 304, other than the exit button, while the visit screen is displayed, the user may perform further user actions after the button is pressed, as indicated feedback arrows in FIG. 5.

Figure 6:
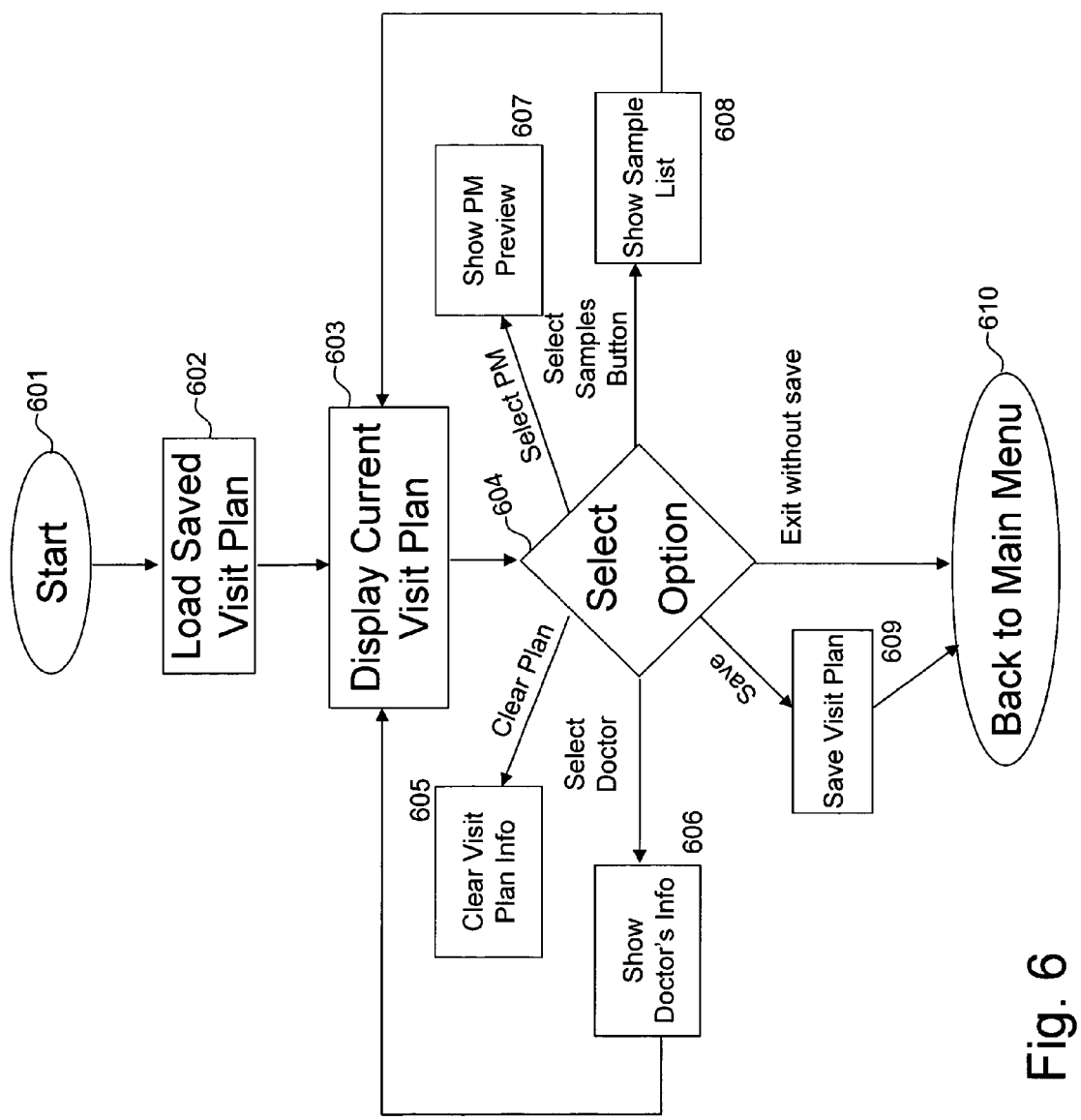

Referring to FIG. 6, in the "plan visit screen," a saved visit plan is loaded (602) and displayed as a "current visit plan" (603). The user is then presented with various options (604). When presented with the various options, the user can select a promotional message, e.g., from a list of promotional messages, to show a preview of the selected promotional message (607). The user can also clear information from the current visit plan, e.g., by pressing a button (605). The user can select a healthcare professional from a list of healthcare professionals to include information about the healthcare professional in the visit plan (606). The user can select samples from a sample list, to include the samples in the visit plan (608). Finally, the user can either save the visit plan and exit the plan visit screen (609), or simply exit the plan visit screen, to return to the main menu screen (610). Typically, the last visit plan that was saved and any information contained therein is displayed in the main menu screen in step (402).

Figure 7:
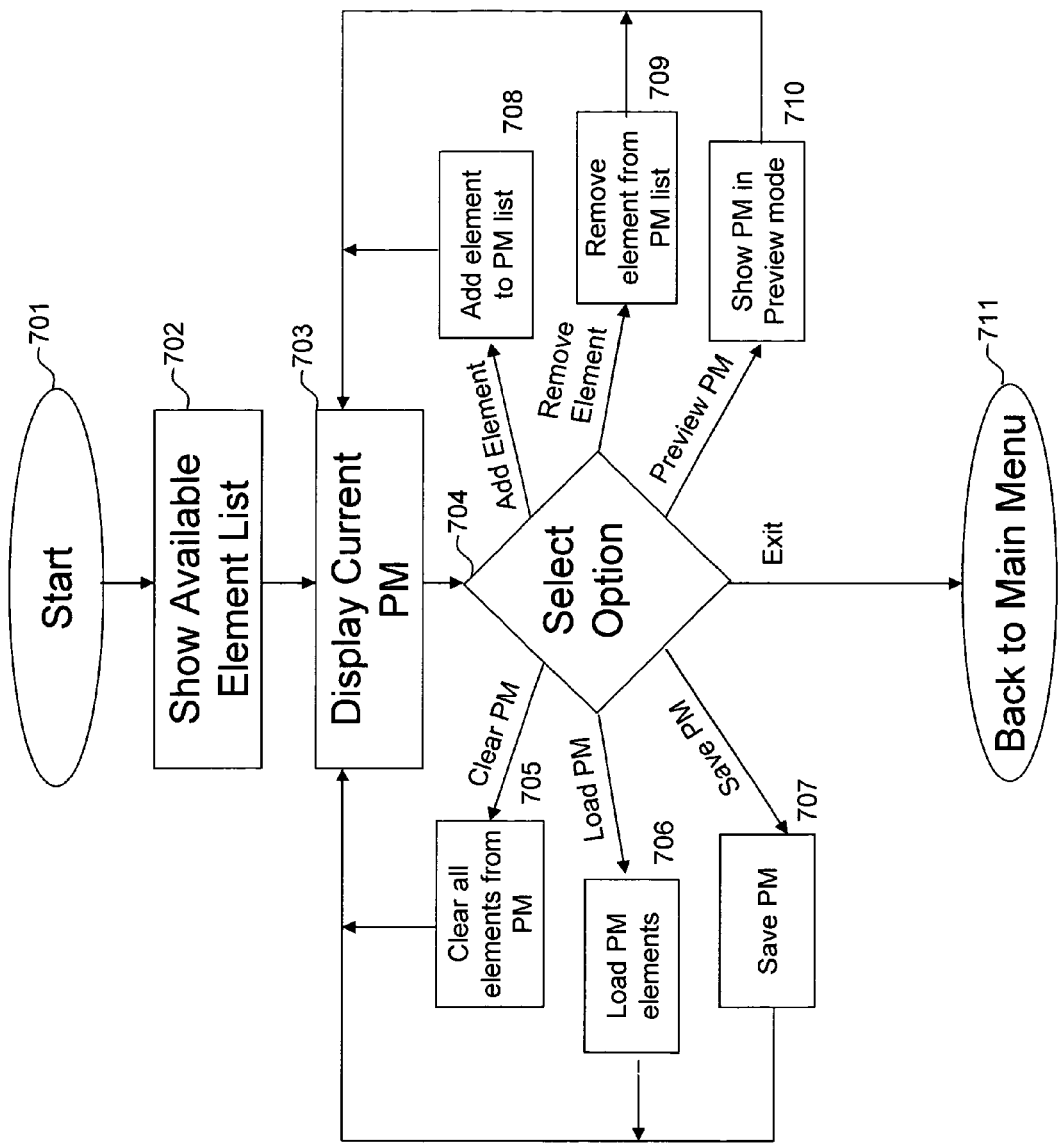

Referring to FIG. 7, in the "build promotional message screen," the user is shown a list of available elements for a promotional message (702), and the user is also shown a current promotional message (702). The user is permitted to select one of various options to in the build promotional message screen to create a custom promotional message or modify the current promotional message. For instance, the user can clear the current promotional message (705), add or remove an element to the current promotional message (708, 709), show a preview of the current promotional message (710), load a new promotional message as the current promotional message (706), or save the current promotional message (707). Finally, the user can exit the build promotional message screen to go back to the main menu screen (711).

Figure 8:
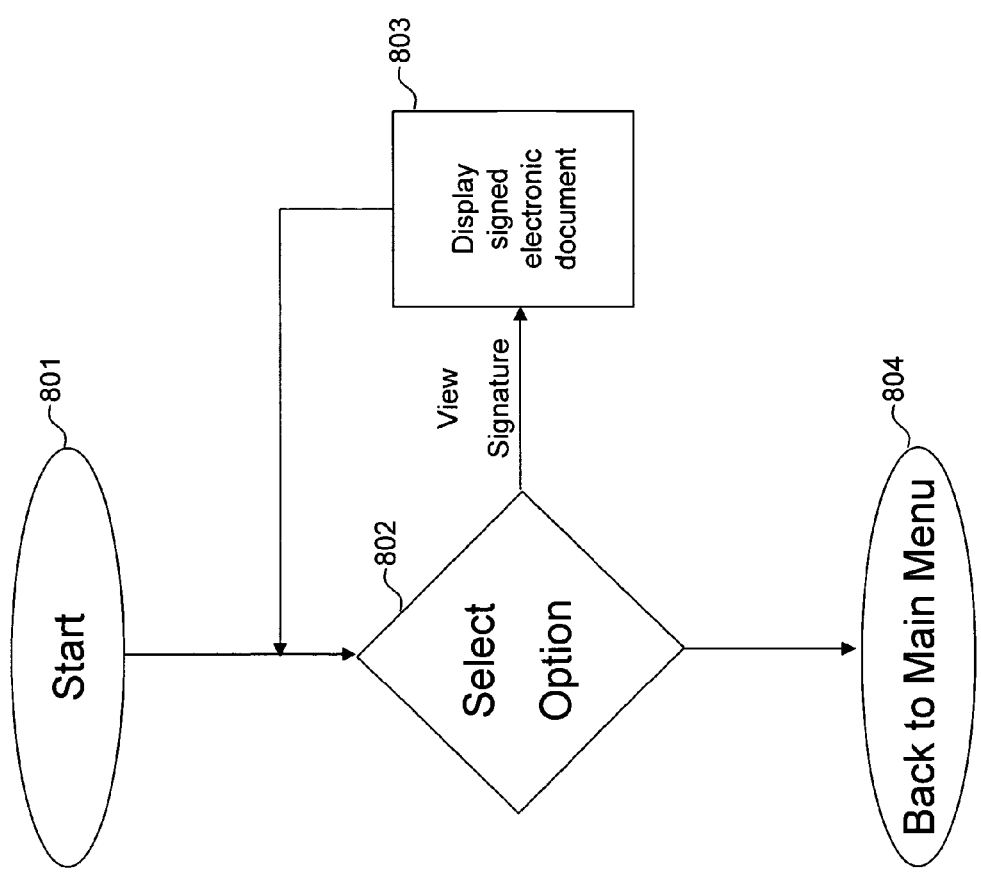

Referring to FIG. 8, in the "view signatures screen," the user can select (802) to view a signed electronic document (803) or exit back to the main menu screen (804).

Figure 9:
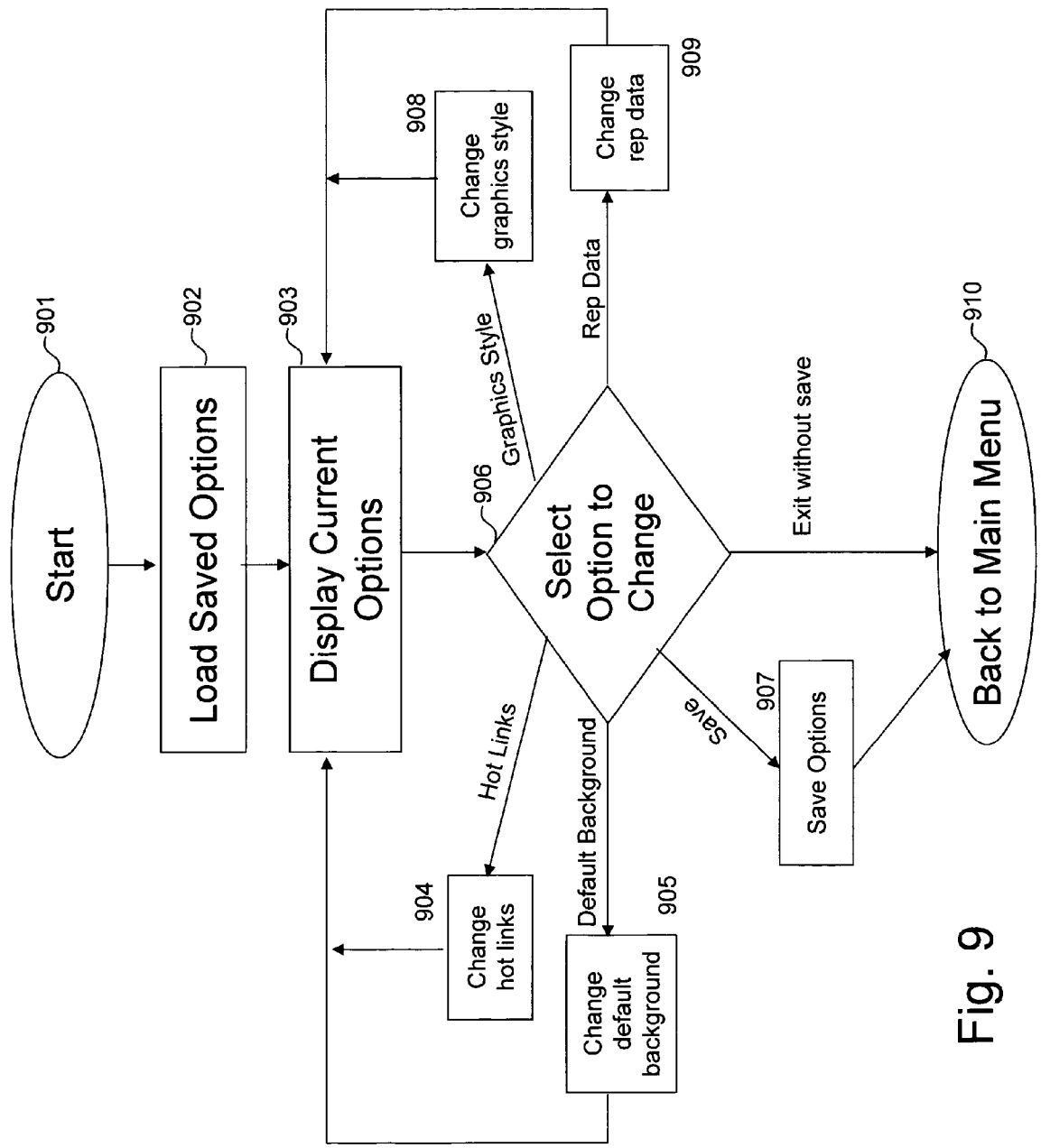

Referring to FIG. 9, in the "options screen," a set of saved options is loaded (902). Initially, the saved options are displayed as "current options" (903). The user can then choose to change one or more of the current options (906). For instance, the user can change the graphics style of whatever is displayed on signature capture device 300 (908), the user can change information about a pharmaceutical representative (909), the user can change what hot links are available from the various different screens (904), and the user can also change the default background of signature capture device

300 (909). Finally, the user can exit the options screen back to the main menu screen, with or without saving (907) any options that were changed.

In any of the screens described in relation to FIGS. 4 through 9, data can be loaded either from a local memory on the signature capture device or from a remote source, i.e., over a network connection. In addition, many of the functions performed manually through each of the screens could also be performed from another device or through some automatic process. For example, information about a healthcare professional or representative may be downloaded to signature capture device 300 over a network.

The input/output functions of signature capture device 300, in particular, the signature capture and display functions, could be embodied in different ways in accordance with the definitions of "signature", "sign", "promotional message", "display", and so forth, as presented above. For example, instead of requiring a healthcare professional to sign with a stylus in the signature block of signature area 302, the healthcare professional could instead enter a fingerprint, a voice print, an electronic signature, etc.

Although the above embodiments principally describe signature capture operations used to capture a healthcare professional's signature for drug samples, similar operations may be used to capture signatures for other purposes. For instance, a signature capture device could be used to capture a healthcare professional's signature when he/she requests proprietary information from the pharmaceutical company. Any time a healthcare professional must sign a signature capture device for any reason, the signing operation may be associated with an opportunity to communicate a promotional message in accordance with embodiments of the invention.

The foregoing embodiments may be implemented by those of ordinary skill in the art using conventional computational platforms, such as a tablet PC, a PDA, a laptop PC, or similar customized device, as a signature capture device. A conventional microprocessor and related memory system may serve to execute and store the application(s) implementing the foregoing methods. The actual construction of such applications is a matter of design choice in view of all of the foregoing.

The preferred embodiments described herein are teaching examples. The scope of the invention is not limited to only these example. Rather, those of ordinary skill in the art will understand that various changes in form and details, as well as extensions of the foregoing teachings may be made to the exemplary embodiments without departing from the scope of the present invention as defined by the following claims.

What is claimed:

1. A method of communicating a promotional message to a healthcare professional, the method comprising:
    providing a drug sample from a pharmaceutical representative to the healthcare professional and in conjunction with providing the drug sample, passing a portable signature capture device from the pharmaceutical representative to the healthcare professional, wherein the signature capture device stores promotional information data including the promotional message;
    capturing signature data from the healthcare professional in the signature capture device; and
    during at least a time period in which the signature data is being captured by the signature capture device to acknowledge receipt of the drug sample by the healthcare professional, communicating the promotional message to the healthcare professional through the signature capture device,
    wherein the stored promotional information data comprises a collection of promotional messages and communicating the promotional message to the healthcare professional comprises selecting the promotional message from the collection of promotional messages based on an automated procedure in view of centralized information related to at least one of the drug sample and the healthcare professional.

2. The method of claim 1, wherein the signature data constitutes a legal acknowledgement required to obtain the drug sample.

3. The method of claim 2, wherein the legal acknowledgement recognizes terms contained in a Drug Information Services Request, an Adverse Reaction Report, or a Drug Interaction Report.

4. The method of claim 2, wherein the healthcare professional is a physician.

5. The method of claim 1, wherein communicating the promotional message to the healthcare professional through the signature capture device comprises displaying the promotional message on a display interface of the signature capture device.

6. The method of claim 5, wherein displaying the promotional message on the display interface begins following a delay after beginning receipt of the signature data.

7. The method of claim 5, wherein displaying the promotional message on the display interface begins before beginning receipt of the signature data and continues while receiving signature data.

8. The method of claim 1, wherein the signature capture device comprises a tablet computer, a personal digital assistant (PDA), or a laptop computer.

9. The method of claim 8, wherein the signature capture device comprises a signature interface, and a display interface configured to display the promotional message in response to a stylus contacting the signature interface.

10. The method of claim 5, wherein displaying the promotional message comprises:
    communicating at least one of text, graphics, and video through the display interface of the signature capture device.

11. The method of claim 10, wherein the promotional message comprises an interactive promotional message and the method further comprises:
    receiving interactive user input from the healthcare professional via a user interface area of the signature capture device.

12. The method of claim 11, further comprising:
    displaying specific information through the signature capture device in response to the interactive user input from the healthcare professional.

13. The method of claim 11, further comprising:
    receiving a request for a pharmaceutical product in the signature capture device through the interactive user input received from the healthcare professional.

14. The method of claim 11, wherein receiving the interactive user input comprises, receiving an answer to a survey question in the signature capture device through the interactive user input from the healthcare professional.

15. The method of claim 11, wherein receiving the interactive user input comprises, receiving an acceptance to a pharmaceutical industry event in the signature capture device through the interactive user input from the healthcare professional.

16. The method of claim 1, wherein capturing signature data from the healthcare professional comprises:
    receiving an electronic signature or a biometric signature via a signature interface of the signature capture device.

17. The method of claim 5, wherein the promotional message comprises a static message or a looping message displayed on the display interface.

18. The method of claim 11, wherein the interactive user input received from the healthcare professional comprises user input commands to the signature capture device through at least one of a software programmable button, a physical button, a stylus, a mouse, a microphone, or a network connection.

19. The method of claim 5, wherein displaying the promotional message on the display interface begins upon beginning receipt of the signature data.

20. The method of claim 1, wherein communicating the promotional message to the healthcare professional comprises playing an audio file through a speaker in the signature capture device.

* * * * *